United States Patent [19]

Maki et al.

[11] Patent Number: 5,202,485
[45] Date of Patent: Apr. 13, 1993

[54] PROCESS FOR PREPARING N-ALKYLAMINOPHENOLS

[75] Inventors: Hiroshi Maki; Michihiro Kawasaki; Horishi Shimizu; Yoshiaki Ito, all of Chiba, Japan

[73] Assignee: Sumitomo Chemical Co., Ltd., Osaka, Japan

[21] Appl. No.: 692,437

[22] Filed: Apr. 29, 1991

Related U.S. Application Data

[63] Continuation-in-part of Ser. No. 610,900, Nov. 9, 1990, abandoned.

[30] Foreign Application Priority Data

Nov. 10, 1989 [JP] Japan .................................. 1-293392
Nov. 10, 1989 [JP] Japan .................................. 1-293393

[51] Int. Cl.$^5$ .......................................... C07C 209/26
[52] U.S. Cl. ................................. 564/398; 564/396; 564/397; 564/401; 564/402; 564/471; 564/473; 564/480
[58] Field of Search ............... 564/408, 398, 397, 480, 564/401, 402, 471, 396, 473

[56] References Cited

U.S. PATENT DOCUMENTS 4,792,622 12/1988 Yokota et al. .................. 564/398
4,921,980 5/1990 Rusek .............................. 564/401

FOREIGN PATENT DOCUMENTS 58026844 8/1981 Japan .

*Primary Examiner*—Glennon H. Hollrah
*Assistant Examiner*—Shailendra Kumar
*Attorney, Agent, or Firm*—Sughrue, Mion, Zinn, Macpeak & Seas

[57] ABSTRACT

A process for preparing an N-alkylaminophenol is disclosed, comprising subjecting an aminophenol to reductive alkylation with an aldehyde or a ketone in the presence of an organic solvent and hydrogen, wherein the reductive alkylation is carried out at a temperature of from 20° to 70° C. in the further presence of a catalyst for reduction comprising platinum and at least one metal element selected from metal elements belonging to the IB group, IIB group, IVB group, VB group, and VIB group of the Periodic Table, supported on activated carbon, or comprising palladium and at least one metal element selected from metal elements belonging to the IB group, IIB group, IVB group, VB group and VIB group of the Periodic Table, supported on activated carbon.

7 Claims, No Drawings

PROCESS FOR PREPARING N-ALKYLAMINOPHENOLS

CROSS REFERENCE TO RELATED APPLICATION

This is a continuation-in-part application of Ser. No. 07/610,000, filed Nov. 9, 1990, now abandoned.

FIELD OF THE INVENTION

This invention relates to a process for preparing an N-alkylaminophenol by subjecting an aminophenol to reductive alkylation with an aldehyde or a ketone in the presence of an organic solvent, a catalyst for reduction, and hydrogen.

BACKGROUND OF THE INVENTION

N-Alkylaminophenols are of extreme importance in industry as intermediates for heat-sensitive or pressure-sensitive dyes, xanthene dyes, fluorescent dyes, etc.

It is conventionally known to prepare an N-alkylaminophenol by reductive alkylation of an alkylaminophenol and an aldehyde or a ketone in the presence of an organic solvent, a catalyst for reduction, and hydrogen.

However, the conventional processes have the following disadvantage. As the conventional noble metal catalysts for use in the reductive alkylation, such as platinum or palladium catalysts, have an ability to reduce an aromatic ring when used as such, nuclear hydrogenation of the aromatic ring may be caused as a side reaction depending on the reaction conditions, resulting in a decrease in the yield of the desired N-alkylaminophenols. Industrially, since these catalysts are expensive, generally it is necessary to use them repeatedly, but this has the following industrially serious problems in addition to the nuclear hydrogenation of aromatic ring. First the aminophenol and the aldehyde or ketone are condensed to form a heavy matter. Also the aldehyde or ketone is reduced to increase the by-production of an alcohol.

Of the problems, concerning the by-production of an alcohol, for example, JP-A-57-165349, JP-A-58-26844, and JP-A-58-194843 disclose techniques for suppressing the by-production of an alcohol by adding a solid sulfur compound during the course of the reductive alkylation, or using a platinum sulfide catalyst. (The term "JP-A" as used herein means an "unexamined published Japanese patent application".)

However, though these techniques can suppress the by-production of an alcohol to a some extent, the reductive alkylation as a main reaction is also suppressed at the same time; thus there is a problem that an unstable Schiff's base of an aminophenol is condensed to form a heavy matter. These techniques also have disadvantages that when the catalyst is used repeatedly, the reaction can be controlled only with difficulty due to elimination of sulfur from the catalyst.

Further almost no conventional techniques have been mentioned about a technique for suppressing nuclear hydrogenation of an aromatic ring, especially no technique for suppressing nuclear hydrogenation of an aromatic ring in the preparation of an N-alkylaminophenol has been known.

SUMMARY OF THE INVENTION

An object of this invention is to provide an industrially advantageous process for preparing an N-alkylaminophenol which can suppress undesirable side reactions such as nuclear hydrogenation of an aromatic ring and reaction which forms heavy matters as described above, and which enables a catalyst to be used repeatedly with a high yield of the desired products.

In order to achieve the object mentioned above, the present inventors have made extensive and intensive investigations and then accomplished this invention based on the finding that the above-described object can be attained by using a platinum or palladium catalyst containing a specific metal element selected in the Periodic Table, or a platinum or palladium catalyst having been contact treated with a solution containing a specific metal element selected in the Periodic Table and employing a specific temperature range for the reaction.

That is, a first aspect of this invention concerns a process for preparing an N-alkylaminophenol comprising subjecting an aminophenol to reductive alkylation with an aldehyde or a ketone in the presence of an organic solvent and hydrogen, wherein the reductive alkylation is carried out at a temperature of from 20° to 70° C. in the further presence of a catalyst for reduction comprising platinum and at least one metal element selected from metal elements belonging to the IB group, IIB group, IVB group, VB group, and VIB group of the Periodic Table, supported on activated carbon, or comprising palladium and at least one metal element selected from metal elements belonging to the IB group, IIB group, IVB group, VB group, and VIB group of the Periodic Table, supported on activated carbon.

A second aspect of this invention concerns a process for preparing an N-alkylaminophenol comprising subjecting an aminophenol to reductive alkylation with an aldehyde or a ketone in the presence of an organic solvent and hydrogen, wherein the reductive alkylation is carried out at a temperature of from 20° to 70° C. in the further presence of a platinum or palladium catalyst supported on activated carbon, having been contact treated with a solution containing at least one metal element selected from metal elements belonging to the IB group, IIB group, IVB group, VB group, and VIB group of the Periodic Table.

DETAILED DESCRIPTION OF THE INVENTION

Aminophenols which can be used in this invention include, for example, o-aminophenol, m-aminophenol, and p-aminophenol.

Aldehydes which can be used in this invention include, for example, aliphatic aldehydes such as formaldehyde, acetaldehyde, propionaldehyde, butyraldehyde, and isovaleraldehyde; cyclic aldehydes such as cyclohexanecarboxyaldehyde and furfural; and aromatic aldehydes such as benzaldehyde and p-tolualdehyde.

Ketones which can be used in this invention include, for example, aliphatic ketones such as acetone, 2-butanone, and 4-methyl-2-pentanone; cyclic ketones such as cyclopentanone and cyclohexanone; and aromatic ketones such as acetophenone and p-methylacetophenone.

N-Alkylaminophenols which can be used in this invention include, for example, N-monoalkylaminophenols such as N-ethylamiophenol, N-propylaminophenol, N-butylamino-phenol, N-cyclohexylaminophenol, N-benzylaminophenol, and N-isopropylaminophenol; and N,N-dialkylaminophenols such as N,N-diethylaminophenol, N,N-dibutylaminophenol, N-ethyl- N-isobutylaminophenol, and N-ethyl-N-isoamylaminophenol.

Organic solvents which can be used in this invention include, for example, aliphatic alcohols such as methanol and ethanol.

A catalyst for reduction which can be used in this invention is a platinum or palladium catalyst containing a specific metal element selected in the Periodic Table, or a platinum or palladium catalyst which has been contact treated with a solution containing a specific metal element selected in the Periodic Table.

The term "metal element selected in the Periodic Table" is intended to be at least one metal element selected from the class consisting of IB group, IIB group, IVB group, VB group, and VIB group of the Periodic Table.

Typical examples of such metallic elements include Cu, Zn, Cd, Sn, Pb, As, Sb, Se, and Te, with Pb, Te, Cu, and As being preferable.

The content of the metal in the catalyst is for reduction is preferably in the range of from 0.001 to 0.5 part by weight, more preferably from 0.005 to 0.2 part by weight, per part by weight of platinum or palladium. If it is less than 0.001 part by weight, the effect of suppressing nuclear hydrogenation of an aromatic ring may be insufficient. On the other hand, if it exceeds 0.5 part by weight, the activity of the catalyst for reduction on the reductive alkylation which is the main reaction may be decreased so that the aminophenol and the aldehyde or ketone would are likely condensed to form a heavy matter.

In the present invention, methods using the platinum or palladium catalyst which has been contact treated with a solution containing a specific metal element selected in the Periodic Table as described above are as follows:

(1) a method wherein a catalyst slurry obtained by adding a metal salt containing a metal element selected in the Periodic Table to a slurry comprising an organic solvent and a platinum or palladium catalyst supported on activated carbon for use in the reductive alkylation is used for the reductive alkylation as is, or (2) a method wherein a solid catalyst obtained by filtering the catalyst slurry mentioned in (1) is used for the reductive alkylation.

Typical embodiments will be mentioned as follows:

The method (1) can be carried out by charging a fresh catalyst, or the catalyst which has been used in the reaction and recovered, together with the organic solvent, and then adding the metal salt solely or as a solution in an organic solvent with stirring. This procedure may be carried out either under an inert gas atmosphere, $N_2$-pressurized atmosphere, or $H_2$-pressurized atmosphere. The temperature and the time of the treatment are not specifically limited, but generally the treatment is sufficiently carried out at from room temperature to 90° C. for from 5 minutes to 2 hours. After this contact treatment, it is preferable to treat the resulting catalyst at room temperature and at atmospheric pressure taking into consideration the reductive alkylation to be carried out thereafter.

The method (2) can be carried out by charging a fresh catalyst, or the catalyst which has been used in the reaction and recovered, together with the organic solvent, adding the metal salt solely or as a solution with stirring, and after stirring, recovering a solid catalyst by filtration. This operation may be carried out either under an inert gas atmosphere at atmospheric pressure or under $N_2$-pressurized atmosphere. The temperature and the time of the operation are not specifically limited, but generally the treatment is sufficiently carried out at from room temperature to 90° C. for from 5 minutes to 2 hours.

In the catalyst for reduction which has been contact treated by the method (1) or (2), almost the whole amount of the metal element used in the contact treatment is contained therein.

In the case of the method (2), the solvent to be used for the formation of the catalyst slurry is not necessarily the organic solvent to be used for the reductive alkylation, but it is preferably the same solvent as that used for the reductive alkylation or water taking into consideration the contamination of the reaction system of the reductive alkylation.

As the metal salt used for obtaining the catalyst slurry, oxides, chlorides, bromides, sulfates, nitrates, phosphates, acetates and oxalates of the metal elements selected in the Periodic Table can be used, but from the standpoint of uniform adsorption of the metal element on the platinum or palladium catalyst, acetates are most preferable.

The amount of the metal element to be used for the contact treatment is preferably in the range of from 0.001 to 0.5 part by weight, more preferably from 0.005 to 0.2 parts by weight, per part by weight of platinum or palladium. If it is less than 0.001 part by weight, the effect of suppressing nuclear hydrogenation of an aromatic ring may be insufficient. On the other hand, if it exceeds 0.5 part by weight, the activity of the catalyst for reduction on the reductive alkylation which is the main reaction may be decreased so that the aminophenol and the aldehyde or ketone are likely condensed to form a heavy matter.

The reaction of this invention is a reaction which gives an N-alkylaminophenol from an aminophenol and an aldehyde or a ketone by reductive alkylation in the present of the above-described organic solvent, hydrogen, and catalyst for reduction. The instant reaction may be carried out by feeding the alkylaminophenol, organic solvent, and the catalyst for reduction under hydrogen pressure, continuously feeding the aldehyde or ketone, or feeding them all at once to bring about the reaction. However, from the viewpoint of carrying out the reaction smoothly, the aldehyde or ketone is preferably fed continuously, and it is more preferable to continuously add a small amount of an organic carboxylic acid such as acetic acid corresponding to the feeding of the aldehyde or ketone.

The reaction temperature is in the range of from 20° to 70° C. The object of this invention can be attained first by employing such a relatively low temperature range for the reaction. If the reaction temperature exceeds 70° C., not only the formation of heavy matters remarkably increases, but undesired nuclear hydrogenation increases. A reaction temperature of lower than 20° C. decreases the reaction rate of the desired reaction.

The reaction pressure may be in the range of from 2 to 30 kg/cm$^2$G.

The amount of the catalyst for reduction to be used is preferably in the range of from 0.0001 to 0.02 part by weight, more preferably from 0.001 to 0.01 part by weight, as platinum or palladium in the catalyst, per part by weight of the starting material aminophenol. If it is less than 0.0001 part by weight, the rate of the main reaction becomes unduly slow, and the formation of heavy matters as a side production may be accelerated.

Conversely, if it is more than 0.02 part by weight, the reduction of the aromatic ring having been accelerated. The catalyst for reduction may be used only once, but usually it is used repeatedly on an industrial scale. Particularly, since almost the whole amount of the metal element selected in the Periodic Table remains in the catalyst used herein even after the catalyst has been used once, no special treatment is needed in the case that this catalyst for reduction is used repeatedly, and the effect of this invention can be maintained. In the case of repeatedly using, since there is a loss of the catalyst by finely dividing and a loss of the recovery by filtration, a small amount of the fresh catalyst is supplemented as occasion may demand and used for the next reductive alkylation.

It is also possible to add the metal element selected in the Periodic Table in such an amount as to meet the fresh catalyst to be supplemented.

As described above, an N-alkylaminophenol can be obtained in the process for preparing an N-alkylaminophenol by subjecting an aminophenol to reductive alkylation with an aldehyde or a ketone in the presence of an organic solvent, a catalyst for reduction, and hydrogen according to the present invention while suppressing side reactions such as nuclear hydrogenation of an aromatic ring and a reaction to form heavy matters as described above with a high yield of the desired products. Especially, when the catalyst for reduction is used repeatedly, an N-alkylaminophenol can be prepared with an industrially outstanding advantage.

Now, the present invention will be described in more detail with reference to the working examples, which should not limit the present invention.

EXAMPLE 1

In a 500 cc-volume SUS-made autoclave equipped provided with a stirrer were charged 32.7 g (0.30 mole) of m-aminophenol, 185.5 g of methanol, and 1.6 g of a commercially available catalyst comprising 5% by weight of platinum supported on activated carbon containing 0.1 part by weight of lead per part by weight of platinum, and 67.6 g of a methanol solution containing 45% by weight of acetaldehyde (acetaldehyde content: 0.69 mole) and 0.20 g (0.0033 mole) of acetic acid were introduced over a period of 1 hour under constant conditions of 40° C. and 10 kg/cm²G of hydrogen pressure. After completion of the introduction of acetaldehyde, the mixture was maintained at the same temperature for an additional 150 minutes and allowed to cool. The catalyst was removed by filtration, and the resulting filtrate was analyzed by gas chromatography, liquid chromatography, and GPC (gel permeation chromatography). As a result, it was found to be 100% of the convention of m-aminophenol (calculated by m-aminophenol consumed/m-aminophenol charged × 100), 95.9% of the selectivity of 3-(diethylamino)phenol, 0.5% of the selectivity of a nuclear hydrogenated product of benzene ring (nuclear hydrogenated product: 3-(diethylamino)-2-hexen-1-one), and 2.1% of the selectivity of heavy matters (values of all selectivity being relative to m-aminophenol).

EXAMPLES 2 TO 4

Using a catalyst obtained after being used in Example 1 and then recovered, the reaction was carried out in a similar manner to Example 1. Afterwards, the reaction was carried out using the catalyst recovered again and again, the results being shown in Table 1.

TABLE 1

| Example | Number of times of catalyst used | Yield of DEMP (%) | Yield of nuclear hydrogenated product (%) | Yield of heavy matters (%) |
|---|---|---|---|---|
| 2 | 2 | 95.2 | 2.5 | 1.7 |
| 3 | 3 | 95.8 | 2.1 | 2.0 |
| 4 | 4 | 95.1 | 2.8 | 2.1 |

Note:
DEMP: 3-(Diethylamino)phenol

All the conversion of m-aminophenol was 100%.

EXAMPLES 5 TO 8

The reaction of Examples 1 to 4 was repeated, except that 1.6 g of a commercially available catalyst comprising 5% by weight of platinum supported on activated carbon containing 0.06 part by weight of tellurium per part by weight of platinum. The results are shown in Table 2.

TABLE 2

| Example | Number of times of catalyst used | Yield of DEMP (%) | Yield of nuclear hydrogenated product (%) | Yield of heavy matters (%) |
|---|---|---|---|---|
| 5 | 1 | 96.8 | 0.3 | 2.6 |
| 6 | 2 | 96.3 | 2.1 | 1.3 |
| 7 | 3 | 95.7 | 2.6 | 1.3 |
| 8 | 4 | 96.0 | 2.5 | 1.1 |

Note:
All the conversion of m-aminophenol was 100%.

EXAMPLES 9 TO 12

The reaction of Examples 1 to 4 was repeated, except that 1.6 g of a commercially available catalyst comprising 5% by weight of platinum supported on activated carbon containing 0.15 part by weight of copper per part by weight of platinum. The results are shown in Table 3.

TABLE 3

| Example | Number of times of catalyst used | Yield of DEMP (%) | Yield of nuclear hydrogenated product (%) | Yield of heavy matters (%) |
|---|---|---|---|---|
| 9 | 1 | 93.3 | 0.3 | 5.7 |
| 10 | 2 | 93.8 | 1.3 | 4.0 |
| 11 | 3 | 93.5 | 1.4 | 4.1 |
| 12 | 4 | 93.7 | 1.2 | 4.3 |

Note:
All the conversion of m-aminophenol was 100%.

COMPARATIVE EXAMPLES 1 TO 4

The reaction was carried out by the same operation as in Examples 1 to 4, except that 1.6 g of a catalyst comprising 5% by weight of platinum supported on activated carbon (which is a commercially available product not containing any metal element selected in the Periodic Table) was used as the catalyst. The results are as shown in Table 4.

TABLE 4

| Comp. Example | Number of times of catalyst used | Yield of DEMP (%) | Yield of nuclear hydrogenated product (%) | Yield of heavy matters (%) |
|---|---|---|---|---|
| 1 | 1 | 95.5 | 1.5 | 2.4 |
| 2 | 2 | 87.7 | 8.0 | 2.0 |
| 3 | 3 | 87.1 | 7.4 | 3.0 |

TABLE 4-continued

| Comp. Example | Number of times of catalyst used | Yield of DEMP (%) | Yield of nuclear hydrogenated product (%) | Yield of heavy matters (%) |
|---|---|---|---|---|
| 4 | 4 | 87.5 | 7.7 | 2.6 |

Note:
All the conversion of m-aminophenol was 100%.

EXAMPLES 13 TO 16

3-(Di-n-butylamino)phenol was synthesized by conducting the reaction in the same manner as in Examples 1 to 4, except that 103.8 g of a methanol solution containing 50% by weight of n-butyraldehyde (n-butyraldehyde content: 0.72 mole) was used in place of the methanol solution containing 45% by weight of acetaldehyde and introduced over a period of 1 hour. The results are shown in Table 5.

TABLE 5

| Example | Number of times of catalyst used | Yield of DBMP (%) | Yield of nuclear hydrogenated product (%) | Yield of heavy matters (%) |
|---|---|---|---|---|
| 13 | 1 | 95.1 | 1.3 | 1.6 |
| 14 | 2 | 94.3 | 1.9 | 1.8 |
| 15 | 3 | 94.5 | 1.8 | 1.7 |
| 16 | 4 | 94.6 | 1.7 | 1.7 |

Note:
All the conversion of m-aminophenol was 100%.
DBMP: 3-(Di-n-butylamino)phenol
Nuclear hydrogenated product: 3-(Di-n-butylamino)-2-hexen-1-one

EXAMPLES 17 TO 20

3-(Cyclohexylamino)phenol was synthesized by conducting the reaction in the same manner as in Examples 1 to 4, except that 70.6 g of a methanol solution containing 50% by weight of cyclohexanone (cyclohexanone content: 0.36 mole) was used in place of the methanol solution containing 45% by weight of acetaldehyde and introduced over a period of 30 minutes. The results are shown in Table 6.

TABLE 6

| Example | Number of times of catalyst used | Yield of OCMP (%) | Yield of nuclear hydrogenated product (%) | Yield of heavy matters (%) |
|---|---|---|---|---|
| 17 | 1 | 96.1 | 1.0 | 0.3 |
| 18 | 2 | 95.3 | 2.5 | 0.4 |
| 19 | 3 | 95.5 | 2.3 | 0.5 |
| 20 | 4 | 95.6 | 2.3 | 0.5 |

Note:
All the conversion of m-aminophenol was 100%.
OCMP: 3-(Cyclohexylamino)phenol
Nuclear hydrogenated product: 3-(Cyclohexylamino)-2-hexen-1-one

EXAMPLES 21 TO 24

3-(N-Ethyl-N-isobutylamino)phenol was synthesized by following the procedure of Examples 1 to 4. In a 500 cc-volume SUS-made autoclave equipped with a stirrer were charged 32.7 g (0.30 mole) of m-aminophenol, 185.5 g of methanol, and 1.6 g of a commercially available catalyst comprising 5% by weight of platinum supported on activated carbon containing 0.1 part by weight of lead per part by weight of platinum, and 47.6 g of a methanol solution containing 50% by weight of isobutyraldehyde (isobutyraldehyde content: 0.33 mole) was introduced over a period of 30 minutes at constant conditions of 40° C. and 10 kg/cm$^2$G. After completion of the introduction of isobutyraldehyde, the mixture was maintained at the same temperature for an additional 60 minutes, after which 41.1 g of a methanol solution containing 45% by weight of acetaldehyde (acetaldehyde content: 0.42 mole) and 0.20 g (0.0033 mole) of acetic acid were continuously introduced over a period of 30 minutes. After completion of the introduction of acetaldehyde, the mixture was maintained at the same temperature for an additional 70 minutes and allowed to cool. The catalyst was removed by filtration, and the resulting filtrate was analyzed by gas chromatography, liquid chromatography, and GPC. The catalyst recovered was reused in the next reaction. The results are as shown in Table 7.

TABLE 7

| Example | Number of times of catalyst used | Yield of EBMP (%) | Yield of nuclear hydrogenated product (%) | Yield of heavy matters (%) |
|---|---|---|---|---|
| 21 | 1 | 95.1 | 1.2 | 1.7 |
| 22 | 2 | 94.2 | 2.1 | 1.7 |
| 23 | 3 | 94.2 | 1.9 | 1.5 |
| 24 | 4 | 94.4 | 1.9 | 1.5 |

Note:
All the conversion of m-aminophenol was 100%.
EBMP: 3-(N-Ethyl-N-isobutylamino)phenyl
Nuclear hydrogenated product: 3-(Isobutylamino)-2-hexen-1-one

EXAMPLES 25 TO 28

3-(N-Ethyl-N-isoamylamino)phenol was synthesized by following the procedure of Examples 21 to 24, except that 56.8 g of a methanol solution containing 50% by weight of isovaleraldehyde (isovaleraldehyde content: 0.33 mole) was used in place of the methanol solution containing 50% by weight of isobutyraldehyde and introduced over a period of 30 minutes. The results are shown in Table 8.

TABLE 8

| Example | Number of times of catalyst used | Yield of EAMP (%) | Yield of nuclear hydrogenated product (%) | Yield of heavy matters (%) |
|---|---|---|---|---|
| 25 | 1 | 94.5 | 1.1 | 1.4 |
| 26 | 2 | 93.2 | 2.0 | 1.3 |
| 27 | 3 | 93.4 | 2.1 | 1.2 |
| 28 | 4 | 93.4 | 1.9 | 1.3 |

Note:
All the conversion of m-aminophenol was 100%.
EAMP: 3-(N-Ethyl-N-isoamylamino)phenol
Nuclear hydrogenated product: 3-(Isoamylamino)-2-hexen-1-one

EXAMPLE 29

In a 500 cc-volume SUS-made autoclave equipped with a stirrer were charged 185.5 g of methanol, 1.6 g of a catalyst comprising 5% by weight of platinum supported on activated carbon, and 0.015 g of lead acetate. The mixture was stirred at room temperature for one hour. Thereafter, 32.7 g (0.30 mole) of m-aminophenol was charged, the hydrogen pressure was maintained at 10 kg/cm$^2$, and 67.5 g of a methanol solution containing 45% by weight of acetaldehyde (acetaldehede content: 0.69 mole), and 0.20 g (0.0033 mole) of acetic acid were continuously introduced over a period of 1 hour at 40° C. After completion of the introduction of acetaldehyde, the mixture was maintained at the same temperature for an additional 90 minutes and allowed to cool. The catalyst was removed by filtration, and the resulting filtrate was analyzed by gas chromatography, liquid chromatography, and GPC. As a result, it was found to be 100% of the conversion of m-aminophenol (calculated by m-aminophenol consumed/m-aminophenol charged×100), 94.5% of t selectivity of 3-(diethylamino)phenol, 1.7% of the selectivity of a nuclear hydrogenated product of benzene ring (nuclear hydrogenated product: 3-(diethylamino)-2-hexen-1-one), and 3.4% of the selectivity of heavy matters (values of all selectivity being relative to m-aminophenol).

EXAMPLE 30

The reaction was carried out by a similar procedure to Example 29, except for using a catalyst which had been recovered after being used in Example 29 and without again treating with lead acetate. As a result of the analysis, the conversion of m-aminophenol was 100%, the selectivity of 3-(diethylamino)phenol was 94.5%, the selectivity of a nuclear hydrogenated product of benzene ring was 1.3%, and the selectivity of heavy matters was 2.9%.

COMPARATIVE EXAMPLE 5

The reaction was carried out by a similar procedure to Example 29, except for using a catalyst which had been used in the reaction once without treating with lead acetate and which was not again treated with lead acetate. As a result of the analysis, the conversion of m-aminophenol was 100%, the selectivity of 3-(diethylamino)phenol was 87.8%, the selectivity of a nuclear hydrogenated product of benzene ring was 7.2%, and the selectivity of heavy matters was 3.3%.

COMPARATIVE EXAMPLE 6

The reaction was carried out by a similar procedure to Example 29, except for using the catalyst which had been recovered after being used in Comparative Example 5 and without again treating with lead acetate. As a result of the analysis, the conversion of m-aminophenol was 100%, the selectivity of 3-(diethylamino)phenol was 87.8%, the selectivity of a nuclear hydrogenated product of benzene ring was 7.0%, and the selectivity of heavy matters was 3.5%.

EXAMPLE 31

The reaction was carried out by a similar procedure to Example 29, except that a catalyst prepared as follows was used: a 200 cc-volume glass-made round bottom flask was charged with 1.6 g of a catalyst comprising 5% by weight of platinum supported on activated carbon and 100 g of water to make a catalyst slurry, after which 0.015 g of lead acetate was added, and the mixture was heated at 80° C. for 1 hour with stirring. After cooling the catalyst slurry, it was filtered under aspiration and then washed twice with 50 g of water, after which the solid catalyst was recovered. As a result, the conversion of m-aminophenol was 100%, the selectivity of 3-(diethylamino)phenol was 94.8%, the selectivity of a nuclear hydrogenated product of benzene ring was 2.8%, and the selectivity of heavy matters was 1.7%.

EXAMPLE 32

The reaction was carried out by a similar procedure to Example 29, except for using the catalyst which had been recovered after being used in Example 31 without again treating with lead acetate. As a result of the analysis, the conversion of m-aminophenol was 100%, the selectivity of 3-(diethylamino)phenol was 95.0%, the selectivity of a nuclear hydrogenated product of benzene ring was 3.0%, and the selectivity of heavy matters was 1.5%.

EXAMPLES 33 AND 34

The reaction was carried out twice by following the procedure of Examples 29 and 30, except that the treatment was performed using copper acetate in place of the lead acetate.

EXAMPLES 35 AND 36

The reaction was carried out twice by following the procedure of Examples 29 and 30, except that the treatment was performed using zinc acetate in place of the lead acetate.

EXAMPLES 37 AND 38

The reaction was carried out twice by following the procedure of Examples 29 and 30, except that the treatment was performed using arsenic acetate in place of the lead acetate.

The results of Examples 33 to 38 are shown in Table 9.

TABLE 9

| Example | Yield of DEMP (%) | Yield of Nuclear Hydrogenated Product (%) | Yield of Heavy Matters (%) |
| --- | --- | --- | --- |
| 33 | 92.9 | 1.7 | 4.4 |
| 34 | 92.5 | 1.3 | 3.9 |
| 35 | 92.8 | 2.8 | 2.7 |
| 36 | 93.0 | 3.0 | 2.5 |
| 37 | 91.7 | 3.5 | 3.9 |
| 38 | 92.2 | 3.0 | 4.1 |

Note:
DEMP: 3-(Diethylamino)phenol
All the conversion of m-amiophenol was 100%.

EXAMPLES 39 AND 40

The reaction was carried out twice by following the procedure of Examples 29 and 30, except that 103.8 g of a methanol solution containing 50% by weight of n-butyrardehyde (n-butyraldehyde content: 0.72 mole) was used in place of the methanol solution containing 45% by weight of acetaldehyde. The results are shown in Table 10.

TABLE 10

| Example | Yield of DBMP (%) | Yield of Nuclear Hydrogenated Product (%) | Yield of Heavy Matters (%) |
| --- | --- | --- | --- |
| 39 | 94.5 | 1.5 | 1.7 |
| 40 | 94.3 | 1.6 | 2.0 |

Note:
DBMP: 3-(Di-n-butylamino)phenol
Nuclear hydrogenated product: 3-(Di-n-butylamino)-2-hexen-1-one All the conversion of m-aminophenol was 100%.

EXAMPLES 41 and 42

The reaction was carried out twice by following the procedure of Examples 29 and 30, except that 70.6 g of a methanol solution containing 50% by weight of cyclohexanone (cyclohexanone content: 0.72 mole) was used in place of the methanol solution containing 45% by weight of acetaldehyde. The results are shown in Table 11.

TABLE 11

| Example | Yield of OCMP (%) | Yield of Nuclear Hydrogenated Product (%) | Yield of Heavy Matters (%) |
| --- | --- | --- | --- |
| 41 | 95.5 | 2.5 | 0.4 |
| 42 | 95.7 | 2.3 | 0.5 |

Note:
OCMP: 3-(Cyclohexylamino)phenol
Nuclear hydrogenated product: 3-(Cyclohexylamino)-2-hexen-1-one All the conversion of m-aminophenol was 100%.

EXAMPLES 43 AND 44

3-(N-Ethyl-N-butylamino)phenol was synthesized by following the procedure of Examples 29 and 30. In a 500 cc-volume SUS-made autoclave equipped with a stirrer were charged 185.5 g of methanol, 1.6 g of a catalyst comprising 5% by weight of platinum supported on activated carbon, and 0.015 g of lead acetate, and the mixture was stirred at room temperature for one hour. Thereafter, 32.7 g (0.30 mole) of m-aminophenol was charged, the hydrogen pressure was maintained at 10 kg/cm$^2$, and 47.6 g of a methanol solution containing isobutyraldehyde (isobutyraldehyde content: 0.33 mole) was continuously introduced over a period of 30 minutes at 40° C. After completion of the introduction of isobutyraldehyde, the mixture was maintained at the same temperature for an additional 1 hour, after which 41.1 g of a methanol solution containing 45% by weight of acetaldehyde (acetaldehyde content: 0 42 mole), and 0.20 g (0.0033 mole) of acetic acid were continuously introduced over a period of 30 minutes. After completion of the introduction of acetaldehyde, the mixture was maintained at the same temperature for an additional 70 minutes and allowed to cool. The filtrate obtained by removing the catalyst by filtration was analyzed by gas chromatography, liquid chromatography, and GPC. The results are shown in Table 12.

TABLE 12

| Example | Yield of EBMP (%) | Yield of Nuclear Hydrogenated Product (%) | Yield of Heavy Matters (%) |
| --- | --- | --- | --- |
| 43 | 94.2 | 2.1 | 1.7 |
| 44 | 94.5 | 1.9 | 1.5 |

Note:
EBMP: 3-(N-Ethyl-N-isobutylamino)phenol
Nuclear hydrogenated product: 3-(Isobutylamino)-2-hexen-1-one All the conversion of m-aminophenol was 100%.

EXAMPLES 45 AND 46

The reaction was carried out twice by following the procedure of Examples 43 and 44, except that 56.8 g of a methanol solution containing 50% by weight of isovaleraldehyde (isovaleraldehyde content: 0.33 mole) was used in place of the methanol solution containing 50% by weight of n-butyraldehyde. The results are shown in Table 13.

TABLE 13

| Example | Yield of EAMP (%) | Yield of Nuclear Hydrogenated Product (%) | Yield of Heavy Matters (%) |
| --- | --- | --- | --- |
| 45 | 93.5 | 2.2 | 1.4 |
| 46 | 93.7 | 2.0 | 1.4 |

Note:
EAMP: 3-(N-Ethyl-N-isoamylamino)phenol
Nuclear hydrogenated product: 3-(Isoamylamino)-2-hexen-1-one All conversion of m-aminophenol was 100%.

EXAMPLE 47

The reaction was carried out by following the procedure of Example 30, except that the reaction temperature was changed to 60° C. As a result of the analysis, the conversion of m-aminophenol was 100%, the selectivity of 3-(diethylamino)phenol was 85.5%, the selectivity of 3-(diethylamino)-2-hexen-1-one was 3.2%, and the selectivity of heavy matters was 7.0%.

COMPARATIVE EXAMPLE 7

The reaction was carried out by following the procedure of Example 30, except that the reaction temperature was changed to 80° C. As a result of the analysis, the conversion of m-aminophenol was 100%, the selectivity of 3-(diethylamino)phenol was 70.9%, the selectivity of 3-(diethylamino)-2-hexen-1-one was 7.1%, and the selectivity of heavy matters was 15.1%.

The results of Examples 30 and 47 and Comparative Example 7 are shown in Table 7.

TABLE 14

(Influence of Reaction Temperature)

| Example No. | Reaction Temperature (°C.) | Yield of DEMP (%) | Yield of Nuclear Hydrogenated Product (%) | Yield of Heavy Matters (%) |
| --- | --- | --- | --- | --- |
| Example 30 | 40 | 94.5 | 1.3 | 2.9 |
| Example 47 | 60 | 85.5 | 3.2 | 7.0 |
| Comparative Example 7 | 80 | 70.9 | 7.1 | 15.1 |

Note:
DEMP: 3-(Diethylamino)phenol
Nuclear hydrogenated product: 3-(Diethylamino)-2-hexen-1-one All the conversion of m-aminophenol was 100%

While the invention has been described in detail and with reference to specific embodiments thereof, it will be apparent to one skilled in the art that various changes and modifications can be made therein without departing from the spirit and scope thereof.

What is claimed is:

1. A process for preparing an N-alkylaminophenol comprising subjecting an aminophenol to reductive alkylation with an aldehyde or a ketone in the presence of methanol or ethanol as an organic solvent and hydrogen, wherein the reductive alkylation is carried out at a temperature of from 20° to 70° C. in the further presence of a catalyst for reduction comprising platinum and at least one metal element selected from metal elements belonging to the IB group, IIB group, IVB group, VB group, and VIB group of the Periodic Table, supported on activated carbon, or comprising palladium and at least one metal element selected from metal elements belonging to the IB group, IIB group, IVB group, VB group, and VIB group of the Periodic Table, supported on activated carbon.

2. A process of claim 1, wherein said catalyst for reduction contains the metal element selected from the Periodic Table in an amount in the range of from 0.001 to 0.5 part by weight per part of platinum or palladium.

3. A process of claim 1, wherein the metal element selected from the Periodic Table is lead, tellurium, copper, or arsenic.

4. A process for preparing an N-alkylaminophenol comprising subjecting an aminophenol to reductive alkylation with an aldehyde or a ketone in the presence of methanol or ethanol as an organic solvent and hydrogen, wherein the reductive alkylation is carried out at a temperature of from 20° to 70° C. in the further presence of a catalyst for reduction comprising a platinum or palladium catalyst supported on activated carbon, having been contact treated with a solution containing at least one metal element selected from metal elements belonging to the IB group, IIB group, IVB group, VB group, and VIB group of the Periodic Table.

5. A process of claim 4, wherein the solution to be used in the contact treatment is a solution in which a salt of the metal element of claim 4 selected in the Periodic Table, which is soluble in the organic solvent used in the reductive alkylation or in water, is used.

6. A process of claim 4, wherein the amount of the metal element selected in the Periodic Table used in the contact treatment is in the range of from 0.001 to 0.5 part by weight per part of platinum or palladium.

7. A process of claim 4, wherein the metal element selected in the Periodic Table is lead, tellurium, copper, or arsenic.

* * * * *